(12) United States Patent
Bub et al.

(10) Patent No.: US 6,743,584 B1
(45) Date of Patent: Jun. 1, 2004

(54) MOLECULAR-BIOLOGICAL MARKER FOR ANALYTICAL ELECTRON MICROSCOPY

(75) Inventors: Sabine Bub, Phillipsburg (DE); Helmut Troester, Mannheim (DE); Karsten Richter, Ketsch (DE); Ansgar Haking, Eppelheim (DE); Stefan Raddatz, Heidelberg (DE); Manfred Wiessler, Frankenthal (DE); Eberhard Spiess, Ladenburg (DE); Michael Trendelenburg, Dossenheim (DE)

(73) Assignee: Deutsches Krebsforschungszentrum Stiftung Des Oeffentlichen Rechts, Heidelberg (DE)

( * ) Notice: Subject to any disclaimer, the term of this patent is extended or adjusted under 35 U.S.C. 154(b) by 0 days.

(21) Appl. No.: 09/914,397

(22) PCT Filed: Jan. 7, 2000

(86) PCT No.: PCT/DE00/00116
§ 371 (c)(1),
(2), (4) Date: Mar. 1, 2002

(87) PCT Pub. No.: WO00/40736
PCT Pub. Date: Jul. 13, 2000

(30) Foreign Application Priority Data

Jan. 8, 1999 (DE) .......................................... 199 00 511

(51) Int. Cl.[7] .......................... C12Q 1/68; C12N 15/00
(52) U.S. Cl. ..................... 435/6; 435/471; 435/320.1; 536/23.1; 536/24.1; 536/25.5
(58) Field of Search ............................ 435/6, 471, 488, 435/252.1, 252.3, 252.33, 320.1, 287.2, 288.7; 536/22.1, 23.1, 24.3, 25.5

(56) References Cited

U.S. PATENT DOCUMENTS

| | | | |
|---|---|---|---|
| 5,302,530 A | 4/1994 | Klein et al. | |
| 5,595,878 A | 1/1997 | Sood et al. | |

FOREIGN PATENT DOCUMENTS

| | | |
|---|---|---|
| DE | 198 03 206 C1 | 6/1999 |
| EP | 0 854 197 A2 | 7/1998 |

OTHER PUBLICATIONS

No additional references are cited by the Examiner.*
Mikhail F. Alexeyev et al., "Improved antibiotic–resistance gene cassettes and omega elements for *Escherichia coli* vector construction and in vitro deletion/insertion mutagenesis", Gene, 1995, pp. 63–67, vol. 160.
H. Troester, "Artificial sequence, fragment from B1 KS (+) 27=SK containing SK primer elements", Feb. 2, 1999, Database Genembl Online!.
Moise Bendayan et al., "Electron Spectroscopic Imaging for High Resolution Immunocytochemistry: Use of Boronated Protein A", The Journal of Histochemistry and Cytochemistry, pp. 573–579, 1989.

Richard T. Giberson et al., "The Influence of Immunogold Particle Size on Labeling Density", Microscopy Research and Technique, 1994, pp. 355–357, vol. 27.
Ute Golla et al., "Theoretical and Experimental Investigations of Resolution and Detection Limits in Energy–Filtering Electron Microscopy", Micron, 1997, pp. 397–406, vol. 28, No. 5.
Subhash C. Gupta et al., "Biological Limitations on the Length of Highly Repetitive DNA Sequences that May be Stably Maintained Within Plasmid Replicons in *Escherichia coli*", Bio/Technology, Sep. 1983.
M.J. Hendzel et al., "Probing Nuclear Ultrastructure by Electron Spectroscopic Imaging", Journal of Microscopy, Apr. 1996, pp. 1–14, vol. 182, pt. 1.
Bernd Hofer, "Construction and Stability of a Sixfold Repeated Artificial Gene", Eur. J. Biochem., 1987, pp. 307–313, vol. 167.
Tomas Kempe et al., "Multiple–copy genes: production and modification of monomeric peptides from large multimeric fusion proteins", Gene, 1985, pp. 239–245, vol. 39.
M.M. Kessels et al., "Immunocytochemistry by Electron Spectroscopic Imaging Using Well Defined Boronated Monovalent Antibody Fragments", Scanning Microscopy Supplement, 1996, pp. 327–344, vol. 10.
Marek Malecki et al., "Preparation of Plasmid DNA in Transfection Complexes for Fluorescence and Electron Spectroscopic Imaging", Scanning Microscopy Supplement, 1996, pp. 1–16, vol. 10.
M.G. Marinus et al., "Isolation of Deoxyribonucleic Acid Methylase Mutants of *Escherichia coli* K–12", Journal of Bacteriology, Jun. 1973, pp. 1143–1150, vol. 114, No. 3.
Current Protocols in Molecular Biology, vol. 1, Copyright 1994–1998 by John Wiley & Sons, Inc.
J. Sambrook, "Molecular Cloning A Laboratory Manual", Second Edition, Cold Spring Laboratory Press (1989).
"Electron Microscopy in Molecular Biology A Practical Approach", J. Somerville et al. (eds), IRL Press, 1987.
Michael F. Trendelenburg et al., "Visualizing Active Genes", Electron Microscopy in Molecular Biology, 1987, pp. 101–146.
B. Qualmann et al., "Electron Spectroscopic Imaging of Antigens by Reaction with Boronated Antibodies", Journal of Microscopy, Jul. 1996, pp. 69–77, vol. 183, Pt. 1.

* cited by examiner

*Primary Examiner*—James Ketter
*Assistant Examiner*—David Lambertson
(74) *Attorney, Agent, or Firm*—Heller Ehrman White & McAuliffe (57) ABSTRACT

The invention relates to plasmids derived from pBluescript KS(+), which contains more than 1, preferably 2, 7, 14, 21 and 27, respective SK primer elements, and their use in analytical electron microscopy.

12 Claims, 6 Drawing Sheets

```
AGCTCGAAATTAACCCTCACTAAAGGGAACAAAAGCTGGTACCGGCCGGATCCACTAGTTCTAGAGCGATCTGATCCACT
+----+----+----+----+----+----+----+----+----+----+----+----+----+----+----+----+ 80
TCGAGCTTTAATTGGGAGTGATTTCCCTTGTTTTCGACCATGGCCGGCCTAGGTGATCAAGATCTCGCTAGACTAGGTGA

AGTTCTAGAGCGATCTGATCCACTAGTTCTAGAGCGATCTGATCCACTAGTTCTAGAGCGATCTGATCCACTAGTTCTAG
+----+----+----+----+----+----+----+----+----+----+----+----+----+----+----+----+ 160
TCAAGATCTCGCTAGACTAGGTGATCAAGATCTCGCTAGACTAGGTGATCAAGATCTCGCTAGACTAGGTGATCAAGATC

AGCGATCTGATCCACTAGTTCTAGAGCGATCTGATCCACTAGTTCTAGAGCGGCCGGATCCACTAGTTCTAGAGCGATCT
+----+----+----+----+----+----+----+----+----+----+----+----+----+----+----+----+ 240
TCGCTAGACTAGGTGATCAAGATCTCGCTAGACTAGGTGATCAAGATCTCGCCGGCCTAGGTGATCAAGATCTCGCTAGA

GATCCACTAGTTCTAGAGCGATCTGATCCACTAGTTCTAGAGCGATCTGATCCACTAGTTCTAGAGCGATCTGATCCACT
+----+----+----+----+----+----+----+----+----+----+----+----+----+----+----+----+ 320
CTACCTCATCAACATCTCGCTAGACTAGGTGATCAAGATCTCGCTAGACTAGGTGATCAAGATCTCGCTAGACTAGGTGA

AGTTCTAGAGCGATCTGATCCACTAGTTCTAGAGCGATCTGATCCACTAGTTCTAGAGCGGCCGGATCCACTAGTTCTAG
+----+----+----+----+----+----+----+----+----+----+----+----+----+----+----+----+ 400
TCAAGATCTCGCTAGACTAGGTGATCAAGATCTCGCTAGACTAGGTGATCAAGATCTCGCCGGCCTAGGTGATCAAGATC

AGCGATCTGATCCACTAGTTCTAGAGCGATCTGATCCACTAGTTCTAGAGCGATCTGATCCACTAGTTCTAGAGCGACTC
+----+----+----+----+----+----+----+----+----+----+----+----+----+----+----+----+ 480
TCGCTAGACTAGGTGATCAAGATCTCGCTAGACTAGGTGATCAAGATCTCGCTAGACTAGGTGATCAAGATCTCGCTAGA

GATCCACTAGTTCTAGAGCGATCTGATCCACTAGTTCTAGAGCGATCTGATCCACTAGTTCTAGAGCGATCTGATCCACT
+----+----+----+----+----+----+----+----+----+----+----+----+----+----+----+----+ 560
CTAGGTGATCAAGATCTCGCTAGACTAGGTGATCAAGATCTCGCTAGACTAGGTGATCAAGATCTCGCTAGACTAGGTGA

AGTTCTAGAGCGATCTGATCCACTAGTTCTAGAGCGATCTGATCCACTAGTTCTAGAGCGATCTGATCCACTAGTTCTAG
+----+----+----+----+----+----+----+----+----+----+----+----+----+----+----+----+ 640
TCAAGATCTCGCTAGACTAGGTGATCAAGATCTCGCTAGACTAGGTGATCAAGATCTCGCTAGACTAGGTGATCAAGATC

AGCGATCTGATCCACTAGTTCTAGAGCGATCTGATCCACTAGTTCTAGAGCGGCCGCCACCGCGGTGGAGCTCCAAT
+----+----+----+----+----+----+----+----+----+----+----+----+----+----+----- 717
TCGCTAGACTAGGTGATCAAGATCTCGCTAGACTAGGTGATCAAGATCTCGCCGGCGGTGGCGCCACCTCGAGGTTA
```

FIG. 5

DETAIL:

SPACER

SEQUENCE LISTING

```
<160> NUMBER OF SEQ ID NOS: 13

<210> SEQ ID NO 1
<211> LENGTH: 717
<212> TYPE: DNA
<213> ORGANISM: Artificial Sequence
<220> FEATURE:
<223> OTHER INFORMATION: Plasmid with 27x SK primer

<400> SEQUENCE: 1
agctcgaaat taaccctcac taaagggaac aaaagctggt accggccgga tccactagtt      60
ctagagcgat ctgatccact agttctagag cgatctgatc cactagttct agagcgatct    120
gatccactag ttctagagcg atctgatcca ctagttctag agcgatctga tccactagtt    180
ctagagcgat ctgatccact agttctagag cggccggatc cactagttct agagcgatct    240
gatccactag ttctagagcg atctgatcca ctagttctag agcgatctga tccactagtt    300
ctagagcgat ctgatccact agttctagag cgatctgatc cactagttct agagcgatct    360
gatccactag ttctagagcg gccggatcca ctagttctag agcgatctga tccactagtt    420
ctagagcgat ctgatccact agttctagag cgatctgatc cactagttct agagcgatct    480
gatccactag ttctagagcg atctgatcca ctagttctag agcgatctga tccactagtt    540
ctagagcgat ctgatccact agttctagag cgatctgatc cactagttct agagcgatct    600
gatccactag ttctagagcg atctgatcca ctagttctag agcgatctga tccactagtt    660
ctagagcgat ctgatccact agttctagag cggccgccac cgcggtggag ctccaat       717

<210> SEQ ID NO 2
<211> LENGTH: 26
<212> TYPE: DNA
<213> ORGANISM: Artificial Sequence
<220> FEATURE:
<223> OTHER INFORMATION: SK primer

<400> SEQUENCE: 2
ggggatccac tagttctaga gcggcc                                           26
```

```
<210> SEQ ID NO 3
<211> LENGTH: 38
<212> TYPE: DNA
<213> ORGANISM: Artificial Sequence
<220> FEATURE:
<223> OTHER INFORMATION: MCS SK primer

<400> SEQUENCE: 3
gtaccgatcg gatccactag ttctagagcg atctgatc                           38

<210> SEQ ID NO 4
<211> LENGTH: 59
<212> TYPE: DNA
<213> ORGANISM: Artificial Sequence
<220> FEATURE:
<223> OTHER INFORMATION: Insertion in plasmid with 2x SK primer

<400> SEQUENCE: 4
gggtaccgat cggatccact agttctagag cgatctgatc cactagttct agagcggcc   59

<210> SEQ ID NO 5
<211> LENGTH: 20
<212> TYPE: DNA
<213> ORGANISM: Artificial Sequence
<220> FEATURE:
<223> OTHER INFORMATION: SK primer

<400> SEQUENCE: 5
gatccactag ttctagagcg                                               20

<210> SEQ ID NO 6
<211> LENGTH: 18
<212> TYPE: DNA
<213> ORGANISM: Artificial Sequence
<220> FEATURE:
<223> OTHER INFORMATION: M13 primer

<400> SEQUENCE: 6
tgtaaaacga cggccagt                                                 18

<210> SEQ ID NO 7
<211> LENGTH: 18
<212> TYPE: DNA
<213> ORGANISM: Artificial Sequence
<220> FEATURE:
<223> OTHER INFORMATION: M13 primer

<400> SEQUENCE: 7
caggaaacag ctatgacc                                                 18

<210> SEQ ID NO 8
<211> LENGTH: 20
<212> TYPE: DNA
<213> ORGANISM: Artificial Sequence
<220> FEATURE:
<223> OTHER INFORMATION: T3 primer

<400> SEQUENCE: 8
aattaaccct cactaaaggg                                               20

<210> SEQ ID NO 9
<211> LENGTH: 20
<212> TYPE: DNA
<213> ORGANISM: Artificial Sequence
<220> FEATURE:
<223> OTHER INFORMATION: T7 primer
```

```
-continued

<400> SEQUENCE: 9
taatacgact cactataggg                                                    20

<210> SEQ ID NO 10
<211> LENGTH: 34
<212> TYPE: DNA
<213> ORGANISM: Artificial Sequence
<220> FEATURE:
<223> OTHER INFORMATION: Insertion in plasmid with 7x SK primer

<400> SEQUENCE: 10
agttctagag cggccgccac cgcggtggag ctcc                                    34

<210> SEQ ID NO 11
<211> LENGTH: 42
<212> TYPE: DNA
<213> ORGANISM: Artificial Sequence
<220> FEATURE:
<223> OTHER INFORMATION: Insertion in plasmid with 7x SK primer

<400> SEQUENCE: 11
gtaccggccg gatccactag ttctagagcg atctgatcca ct                           42

<210> SEQ ID NO 12
<211> LENGTH: 48
<212> TYPE: DNA
<213> ORGANISM: Artificial Sequence
<220> FEATURE:
<223> OTHER INFORMATION: Insertion in plasmid with 14x SK primer

<400> SEQUENCE: 12
atctgatcca ctagttctag agcggccgga tccactagtt ctagagcg                     48

<210> SEQ ID NO 13
<211> LENGTH: 20
<212> TYPE: DNA
<213> ORGANISM: Artificial Sequence
<220> FEATURE:
<223> OTHER INFORMATION: SK oligonucleotide

<400> SEQUENCE: 13
cgctctagaa ctagtggatc                                                    20
```

MOLECULAR-BIOLOGICAL MARKER FOR ANALYTICAL ELECTRON MICROSCOPY

This application receives priority from application PCT/DE00/00116, filed Jan. 7, 2001, which claims priority to German Patent Application No. 199 00 511.7, filed Jan. 7, 1999, the entireties of which are hereby incorporated by reference.

BACKGROUND OF THE INVENTION

The invention relates to plasmids derived from pBluescript KS(+), comprising more than 1 SK primer sequence element, preferably 2, 7, 14, 21 and 27 repetitive SK primer sequence elements, and their use as molecular-biological markers in analytical electron microscopy.

Electron spectroscopic imaging (ESI) is a method of analytical electron microscopy (EM), which pictures the distribution of certain chemical elements within an analyzed preparation. In order to elucidate the structural organizations of biological systems, it must be possible to optically differentiate the individual macromolecular components. At present, charging with, gold particles or other particles, which are visible in refraction contrast, is used to label macromolecules for electron microscopy.

Multiple labeling experiments have been carried out in electron microscopy, where particles of various sizes are used, which enable differentiation of different target structures in a single preparation. For example, one type of molecule is linked to gold particles having a size of 5 nm while another type is linked to 10–20 nm sized particles in a double labeling experiment, to ensure that in a subsequent evaluation different molecules can be clearly localized and distinguished from one another. Large gold particles (larger than 10 nm) are disadvantageous, because of lower penetration capacity into the tissue and reduced coupling efficiency to a target molecule (Giberson, T. R., and Demaree, R. S.: The influence of immunogold particle size on labeling density. Microscopy Research and Technique, 27, 355–357, 1994). In addition, such a large particle is no longer assigned to a binding site of a target structure, because, resolution capability would be lost. If a triple labeling experiment is aimed at, the above drawbacks would become particularly striking. Only ferritin molecules, i.e. large protein units, which contain hundreds of iron atoms in their centers and can be linked to target structures, which are alternative to the gold particles. However, their electron density and detectability under the transmission electron microscope is very poor. Therefore, their use has been proved feasible only in rare cases.

On the other hand, florescence methods enable triple and quadruple labeling without any major problem in optical microscopy. Electron microscopy with the existing labeling techniques could not compete with optical microscopy. Therefore, scientists have been using optical microscopes with comparatively poor resolution capability. The development of an alternative labeling technique for gold labeling would render electron microscopy more attractive, because its advantageous labeling provides a resolution capability over 100 times as good as that of the optical microscopy. The gold labeling method for conventional transmission electron microscopy is based on the electron density of heavy metal gold and there is a demand for an alternative labeling method for ESI. This technique, which utilizes interactions between beam electrons and the atoms in the preparation, differs from conventional transmission electron microscopy. In principle, all of the elements can be detected specifically, which raises the number of elements in consideration for labeling methods. However, to establish alternative labeling methods, it is decisive to check detection limits for the elements in consideration. This means, information is required on the number of detectable element atoms per $nm^2$ area. Therefore, the detection limits of the ESI technique are relevant. Only a few study-reports and vague indications on this parameter are available. Although the ESI technique is often used, no data on detection limits have been published to date.

There is a demand for alternative labeling methods for electron microscopy. It should be possible to readily test and assess the detectability of a marker complex.

Therefore, an object of the present invention is to provide a method of obtaining data, to evaluate the prospects of the intended experiment with the element in question and/or the marker structure in question, before time-consuming cyto-biological and molecular-biological experiments are carried out. Furthermore, the parameter for the detectable number of elementary atoms per unit area shall become measurable to obtain necessary information to establish EM labeling methods.

This object is achieved by the subject matters defined in the claims section.

Until now, there has been no accurate limiting values of detectability known for the ESI detection of the various chemical elements. This is inter alia due to the fact that preparing a suitable test sample is not a trivial matter. Such a sample must have special properties. There must be regions in which the target element is available in a clearly defined amount. It must be possible to clearly detect these regions. The target element may not occur in the remaining regions. This problem has been reported by investigators who tried to record the resolution and detectability by means of grainy precipitates, using uranium, for example (see, Golla and Kohl, Micron, 28:(5), 397–406, 1997).

BRIEF SUMMARY OF THE INVENTION

In one aspect, the invention provides plasmids derived from pBluescript KS(+), comprising more than 1 SK primer sequence element, preferably 2, 7, 14, 21 and 27 repetitive SK primer sequence elements.

In another aspect, the invention provides methods of analytical electron microscopy, comprising: providing the plasmid as described herein; adding a detectable element to the SK primer, thereby forming a marker complex; and imaging the marker complex by electron microscopy.

In yet another aspect, the invention provides a test kit for use in electron microscopy comprising: host *E. coli* JM110 bacterial cells suitable for replicating the plasmid as described herein; and a single-stranded plasmid comprising 2, 7, 14, 21, and 27 repetitive SK primer sequence elements.

BRIEF DESCRIPTION OF THE DRAWINGS

FIG. 1 shows construction of pBl KS(+) containing 2 repetitive SK primers. The multiple cloning site (MCS) and the SK primer sequences are shown in boxes. Restriction sites are marked with broken lines. The figure also shows sequence segments that are important for cloning.

FIG. 1D shows a simplified diagram of pBl KS(+) containing 2 repetitive SK primers. Solid line represents MCS and broken lines indicate the remainder of vector pBl KS(+). Arrows show the 5'→3' direction of the cloned SK primers plus a 4 bp sequence, which is a non-hybridizing fragment (also see FIG. 1C).

FIGS. 3A and 3B show diagram of cloning a pBl containing 2 repetitive block plasmid, FIG. 3A shows Insertion of a 7 repetitive SK block in the Not I- digested pBl 1× block DNA. Descriptions of the individual components are as shown in FIG. 1 or 2. The clone pBl 1× block is linearized with the Not I enzyme and ligated with the PCR fragment subsequently cut by Eag I beforehand.

FIG. 3B (SEQ ID NO:12) shows the transitions between individual blocks. The construction of the components is similar that of FIGS. 1A–1D. By ligation of the 7× SK block (gray arrow) in the proper orientation, the Not I restriction site, which digested the pBl 1× block beforehand is masked by the 5' end of the newly added 7× SK block (bold letters) and could no longer be excised by Not I. The 3' end of the fragment completes the Not I restriction site towards the vector. As a result, it is possible in the subsequent cloning run to linearize the pBl 2× block with Not I without losing the 14 SK primer. In contrast to the BamH I cleavage site between the individual SK primers In the block (BamH I*), the BamH I restriction site at the 5' end of a 7× block is maintained (BamH 1) and can subsequently be used as an orientation control.

DETAILED DESCRIPTION OF THE INVENTION

The invention provides a series of new plasmids having more than 1, preferably 2, 7, 14, 21 and 27, SK primer sequence elements, was produced in direct head/tail-oriented repetition on the basis of pBluescript KS(+). The plasmids present a target structure, which contains repetitively a short DNA sequence (the SK primer sequence element). The SK primer sequence element comprises the following sequence (SEQ ID NO:5):

5'-GATCCACTAGTTCTAGAGCG-3'.

The SK primer (Stratagene) sequence represents a segment of 20 nucleotides in vectors pBluescript KS(+/−) and Bluescript SK (+/−) (Stratagene), which is located within the "multiple cloning site" (MCS) of the vector, pBluescript is a plasmid vector sold by Stratagene. It is a circular DNA molecule that contains genetic materials required for replication in E. coli. The multiple cloning site (MCS) is decisive for cloning foreign DNA segments into the vector. According to an embodiment of the invention the above-mentioned SK primer sequence repetitions were incorporated into the MCS region so that the resulting plasmids of pBluescript only differ in the MCS, i.e. the plasmids are derived from the pBluescript.

A homologous sequence may bind the repetitive sequence by hybridization. In the event, that a hybridizing sequence carries a marker complex, the marker will reach the target structure by hybridization.

The hybridizing sequence, which refers to SK oligonucleotide or SKO, can be modified chemically at its ends to permit a covalent binding of different markers. As a result, it is possible to study any labeling strategies. A molecule can be linked to the SKO containing an element in the highest possible concentration, which should be tested for usability as a marker for ESI. Boron markers, as described in German patent application 198 03 206.4, for example, are suitable. Further promising markers are silicon, iron and manganese. The marker compound is built up in a controlled synthesis such that the number of target elementary atoms is known and the target element is present in the greatest possible amount in the center of the marker compound. It can also be linked to the SKO as a unit. In order to do that, the boron marker structure is synthesized by treating it like a nucleoside unit in the oligonucleotide synthesis, for example. Therefore, the preferred linking system provides the production of a boron compound containing the necessary protective groups and linkage groups for the oligonucleotide synthesis according to the phosphoramidite method. During the process, an oligonucleotide is built up, building block by building block, from the 3' end to the 5' end. There is a possibility that for this purpose the boron complex is attached as such or in the form of a 5'-boron nucleotide(C)-3' building block to the 5' end of SKO at the final step (see German patent application 19803206.4, for example). It is advantageous for the marker-containing building block to contain a spacer which will cause the marker complex to stand off from the SKO so as not to impede the hybridization of the labeled SKO with the complementary plasmid regions. Aliphatic hydrocarbon chains which have lengths between $C_2$ and $C_{10}$ and may possibly contain oxygen groups in the form of ether bridges (preferably a maximum of 5 bridges) are considered as spacers (see German patent application 198 03 206.4, for example). A similar procedure can be used for any other marker structures, containing a target element.

The labeled oligonucleotides are hybridized to the DNA and are present selectively in the preparation at the sites where the circular DNA molecules are located.

Depending on the number of repetitions of the SK elements on the employed plasmid molecules, variable but defined amounts of target elementary atoms is attached to the DNA in a very close arrangement. Therefore, densest packaging can be assumed because it was found that the distances of the marker structures on the DNA are 8 nm. This follows from a calculation of the extension of double-stranded DNA regions over the SK repetition units present in the plasmids. Since the marker structure contains a maximum diameter of 5 nm there is in fact some space available between the markers. However, this space should be maintained because the hydrate envelope of the marker compounds must be taken into account.

The plasmid according to the invention is prepared on the carrier matrix of the sample holder for ESI in linear form. The above plasmids enable the preparation of single-stranded circular plasmid DNA molecules after infecting plasmid-containing *E. coli* cells, preferably *E. coli* JM 110, by a helper virus. The (+) sign in the name of the original plasmid pBluescript KS (+) indicates that only the plus strand of the plasmid molecule is isolated. A single-stranded DNA sample is therefore available to complementary DNA regions, which can be readily hybridized without fusing the DNA duplex. In order to hybridize SK oligonucleotides (SKO) complementary with the plus strand of the plasmids, they must, of course, represent the sequence of the minus strand, i.e. 5'-CGCTCTAGAACTAGTGGATC-3' (SEQ ID NO: 3). Such an oligonucleotide can be produced by an automatic oligonucleotide synthesizer. These molecules are mixed in an aqueous solution with one of the above-mentioned single-stranded plasmid molecules. Double-stranded regions form at the sites where the SK oligonucleotides (SKO) have found the complementary partner on the singled-stranded DNA, i.e. SK oligonucleotide/plasmid hybrids (SKOPH). In order not to impede the binding of the single SKOs to the DNA, a gap of 4 nucleotides is preferably provided as a spacer between the SK oligonucleotide binding sites.

These SKOPHs are preferably separated by the chromatography of unbound SKOs. This may be done by column chromatography, e.g. Amersham Pharmacia Biotech (Freiburg, Germany) offer column matrixes (e.g. sephadex or sepharose). The purified SKOPHs are then subjected to spreading. In this connection otherwise coiled DNA molecules are pretreated such that they are stretched in solution and in this state are applied onto electron-microscopic small carrier nets coated with a thin sheeting, made visible by treatment with heavy metals and analyzed under a transmission electron microscope (TEM). If ESI analysis shall be carried out, heavy metal treatment should be dropped, since every element occurring in high amounts and/or high concentrations in the preparation interferes with, or makes impossible, the specific detection of the target element. The DNA rings are then distributed uniformly over the surface of the TEM preparation and are separate from one another.

When above-mentioned basic preconditions are met: the circular DNA is clearly evident, the SKOs are-available in a more or less large number and are bound to the DNA, and there is (almost) nothing in between the DNA regions.

In case if it is not clear whether the SKOs were bound to the repetitive region or not, there are two possibilities for control: a) SKOs labeled at the 5' position by digoxigenin or biotin are used against which an anti-digoxigenin or an anti-biotin antibody is employed, which itself is labeled with gold and can be detected by conventional TEM. The size of the gold particles may, however, not exceed a diameter of about 6 nm (otherwise the gold particles could interfere with one another); b) the repetitive target plasmid can be linearized, possibly in combination with a), by restriction endonuclease digest along with the repetitive SK region, so that following spreading the binding sites of the SKOs are readily identifiable in that they must be located at the end of a thread-like DNA molecule. Since restriction endonucleases only excise double-stranded DNA, its restriction site must first be made double-stranded by hybridization of an oligonucleotide complementary around the restriction site.

The repetitive sequences are arranged closely one behind the other and extend over about a third of the plasmid. These repetitive sequences render the test much more significant. The advantage of the above described plasmids consists in that 1 to 27 of the marker units can be accumulated so as to modulate the number of marker elementary atoms. When it is possible to show the labeled SKOPHs in differing spreading states from fully extended to coiled in the spreading preparation, the target elementary atoms, bound particularly to coiled DNA molecules, can i) be concentrated within a very confined space, ii) become localizable due to the uniformly fibrillary ring shape of the bound-DNA, iii) be analyzed in defined but variable number, and iv) be in an otherwise element-free environment.

DNA segments outside the repetition regions to which no marker can bind serve as a negative control for the ESI elemental detection. Such a negative control is necessary because the specificity of a calculated target element distribution could be doubted if there were no comparative region without target element and correspondingly without calculated element signal. Since the test represents a molecular-biological system, the marker is assessed in its physico-chemical environment. This also means that the test is very close to a medical/biological application, in particular the in situ hybridization.

It is an objective of this test method to obtain reliable data on the minimum number of target element atoms per unit area necessary for ESI detection. At the same time, data are obtained on the individual detectability of the marker structure and because of the repetition, it is also possible to obtain average weak element-specific signals, in particular, in DNA molecules available in the electron-microscopic preparation in a fully stretched manner. Therefore, it can be determined prior to a technically complicated use of a marker structure in medicine or biology whether optionally the number or/and the concentration of the target elementary atoms must still be increased in the marker structure. All of the plasmid states from stretched to considerably coiled are found in spreading preparations, in particular when the spreading process did not proceed in optimum fashion. This is of advantage in connection with the explained determination of elemental detection limit.

Many variations of spreading methods are found in the literature (see for example. Electron Microscopy in Molecular Biology; a practical approach, Sommerville, J. and Scheer, U. (eds.), IRL Press, 1987).

The threshold values for the element-specific detection can be determined by the standard methods of elemental detection using ESI. For this, there is presently no other method available. Therefore, it can be considered that this method is also of interest for the scientists who do not have a bio-medical application in mind, but are interested in the detection limits of any chemical elements other than those mentioned above. The precondition is that the target element is already present in the marker structure linked to the oligonucleotide in the highest possible concentration and in the greatest possible amount.

The use for ESI is described above. In addition, applications of parts of the test system are also possible, which go beyond the use in electron microscopy. Two additional sample applications are briefly described below: 1) the SK primer repetition cassette can generally be utilized for an efficient and localized DNA labeling by hybridizing with labeled oligonucleotides; and 2) for studying the mechanisms of deleting direct repetitions in DNA, as described below.

In addition to the application in the field of electron microscopy, said repetition regions enable, as stated above, the possibility of also rendering DNA quite generally detectable after the hybridization by means of the SKO-linked markers which are still below the detection limit as single molecules but can be identified in repetitive arrangement. For this purpose, the repetition regions can also be recloned into the desired DNA molecules via SAC I/Kpn I-compatible ends. For example, the route of DNA can then be tracked by such a method after introduction into a cell (transfection). Here, the uses of both optical and electron microscopes are in consideration.

The chemical modifiability of the hybridizing sequence permits different uses of the test for differently configured marker units. Since the test represents a molecular-biological system, the marker is assessed in its physico-chemical environment. The individual detectability of the marker is analyzed. The intensity of weak signals can be determined precisely by averaging.

The following statements made on the production of the plasmids containing different repetitions show that in principle the repetition steps (pBluescript KS (+)) 2×, 3×, 4×, 5×, 6×, 7×, 14×, 21× and 27× SK are available for the experiments for the actual elemental detection for ESI. Since the analysis of differences as to the detectability of the target element using ESI will be especially convincing when the number of analyzed elementary atoms varies considerably (see description below), the number of repetitions repetition degrees 2×, 7×, 21× and 27× SK are of special interest.

As mentioned above, the present invention is based on the fact that a test preparation contains areas in which the target element is available in a clearly defined amount and can be detected unambiguously. The target element may not occur in the remaining areas.

The plasmid construction is stabilized by introduction into a dam⁻/dcm⁻ strain (preferably E. coli JM 110). JM110 is dam⁻/dcm⁻ and contains no other striking genotypic markers, which would clearly distinguish this strain from the other ones used, so that they can be employed as well. The repetitive plasmids according to the invention are introduced into the dam⁻/dcm⁻ strain according to standard methods (cf. Sambrook, J., Fritsch, E. F. and Maniatis, T.: Molecular cloning; A laboratory manual; Second edition, Cold Spring Harbor Laboratory Press (1989)). Surprisingly, a deletion of the directly repetitive elements is avoided during bacterial replication. It is known that the direct repeats or inverted repeats are lost during the replication in E. coli. Dam/dcm strains are documented in the literature (cf. Marinus et al., J. Bacteriol. 114 (3), 1143–1150 (1973)); however, stabilization of directly repetitive sequences has never been described.

The number of repetitions could even be increased to 27× in E. coli JM110. Furthermore, the combination of E. coli JM110/pBl KS (+) 27× SK is a new system in which a direct repetition sequence otherwise unstable in E. coli can be replicated. Bacterial geneticists get the possibility of analyzing the underlying mechanisms of this type of deletions in bacteria and characterize the involved components. The question of stabilizing repetitions of such a type in E. coli is of interest e.g. for cloning specialists who try to obtain human DNA segments in their original state even if they had been replicated in E. coli (see e.g. human genome project). The background is that human DNA segments also contain short directly repetitive segments which like the above-described SK primer sequence repetition can show relatively poor stabilizing characteristics.

The plasmids according to the invention can be combined into test kits for use in electron microscopy. A test kit contains e.g. the following materials: 1) competent E. coli JM110 bacterial cells for replicating the repetitive plasmids; 2) the single-stranded plasmids containing 1×, or 2×, 7×, 14×, 21× and 27× SK for the differential analysis of marker structures for the electron microscope; 3) electron-microscopic small carrier nets which are already coated for spreading: 4) SK oligonucleotides labeled at their 5' end by biotinylation or digoxigenation and serving for optimizing hybridization and spreading by proving by means of a gold-linked anti-biotin or anti-digoxigenin antibody that the repetitive arrangement is actually given on the plasmid; and 5) instructions describing the individual processing steps. If there is an interest in applications other than the ESI-dependent ones, the test kit can be modified.

The plasmids having 2, 7, 14, 21 and 27 SK primer sequence elements were deposited as E. coli cultures with DSMZ (German-type collection of microorganisms and cell cultures), Mascheroder Weg 1, Braunschweig, Germany, under accession numbers DSM 12600, DSM 12601, DSM 12602, DSM 12603, and DSM 12604 on Dec. 22, 1998:

| pBI KS(+)2 × SK | DSM 12600 |
| pBI KS(+)7 × SK | DSM 12601 |
| pBI KS(+)14 × SK | DSM 12602 |
| pBI KS(+)21 × SK | DSM 12603 |
| pBI KS(+)27 × SK | DSM 12604 |

The following example explains the invention in more detail.

EXAMPLE

Methods of producing the plasmids containing the repetitions are well known in the art (see, for example, Sambrook et al., *Molecular cloning; a laboratory manual; second edition*; Cold Spring Harbor Laboratory Press, 1989; and Current Protocols in Molecular Biology, John Wiley and Sons, 1994–1998). These techniques, including, for example, DNA replication, restriction endonuclease digestion, ligation, agarose gel electrophoresis, and PCR, are known to skilled artisans.

The SK primer element of Bluescript was selected for the repetition (Stragene company, Heidelberg, Germany) because it does not contain any self-complementary or homooligomeric regions, with a G/C content of 50%, which lies within the average region of natural DNA and is suited for the almost full production of directly repetitive regions as regards the cloning technique. Furthermore, it is advantageous that this region hybridizes reliably and stably with a complementary sequencing primer (identical with the SK primer) since it has been designed by Stratagene (Heidelberg) as a sequencing primer binding site;

A short oligonucleotide fragment is required for the construction of SK primer sequence elements in repetitive succession. It contains the SK primer sequence and restriction sites for carrying out cloning. For this purpose oligonucleotides complementary to one another were synthesized. These ss-DNA fragments were converted by hybridization into cloneable ds fragments by juxtaposing the two complementary oligonucleotides in equimolar fashion in 10 mM Tris buffer. A successfully obtained clone was used as a control. The resulting fragments were referred to as SK-PH I (SK primer hybrid I; fragment which was used for the SK primer replication of 2–6 SK primer sequences; see FIG. 1) and SK-PH II (SK primer hybrid II; fragment which introduced the seventh SK primer and the Eag I restriction site; see FIG. 2).

Figure 1A:
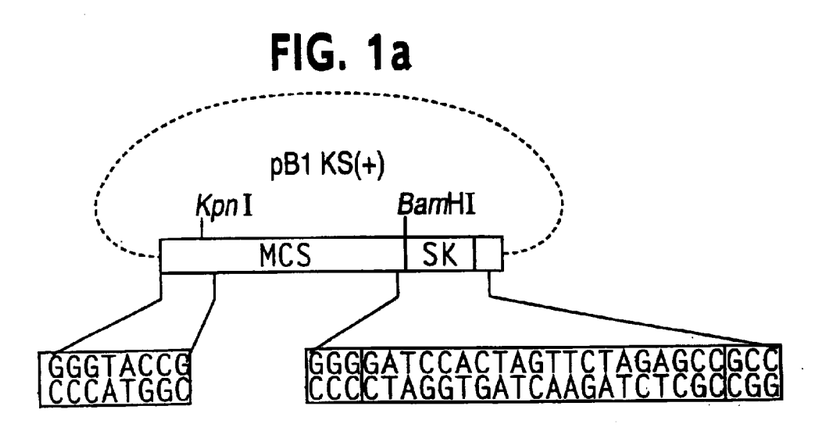
FIG. 1A. Diagram of pBl KS(+) (SEQ ID NO:2): pBl KS(+) is digested with the restriction enzymes Kpn I and BamH I for subsequent cloning. The restriction sites are marked with broken lines. The MCS fragment is flanked by the restriction sites.
Figure 1B:
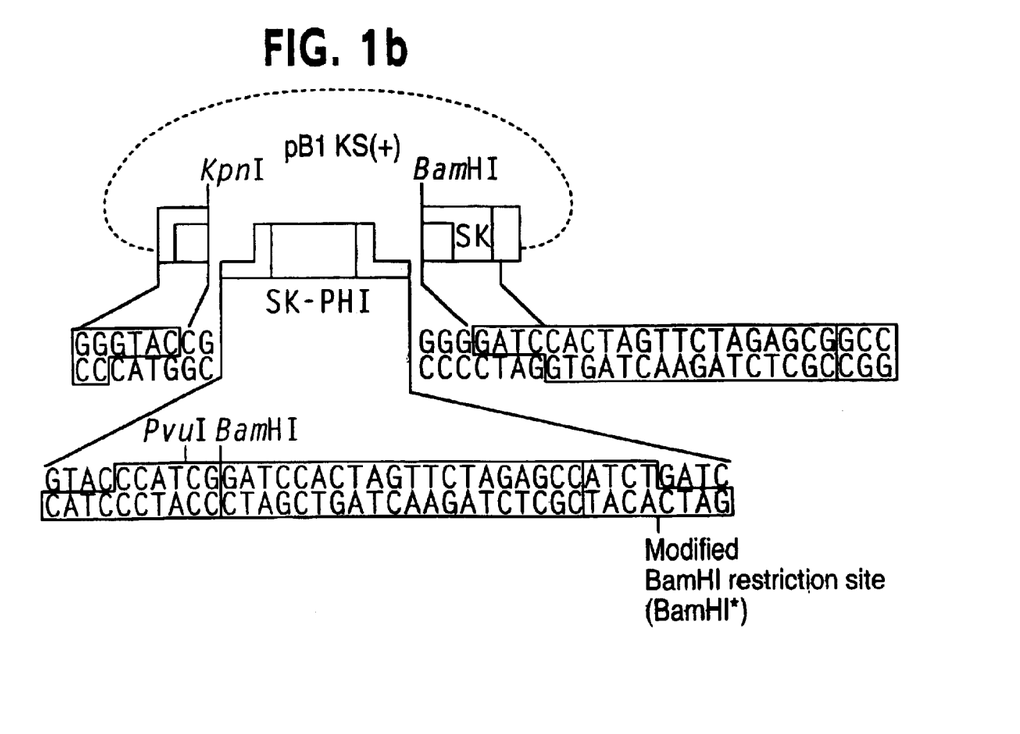
FIG. 1*b* (SEQ ID NOs:2 and 3) shows pBl KS(+) digested with BamH I and Kpn I and a SK-PH I fragment resulting in pBl KS(+) 2 repetitive SK when ligated with pBl KS(+). Part of MCS is excised by digestion with Kpn I and BamH I (also see FIG. 1A), and fragment SK-PH I is inserted. Previously present Bam H I restriction site is masked by SK-PH I via a base pair modification (bold letters) while a new BamH I restriction site is introduced at the same time. Due to the different restriction sites (Kpn I/BamH I), the fragment can be cloned only in one orientation, The restriction site Pvu I served as a control restriction site for the successful incorporation of the insert SK-PH I.
Figure 1C:
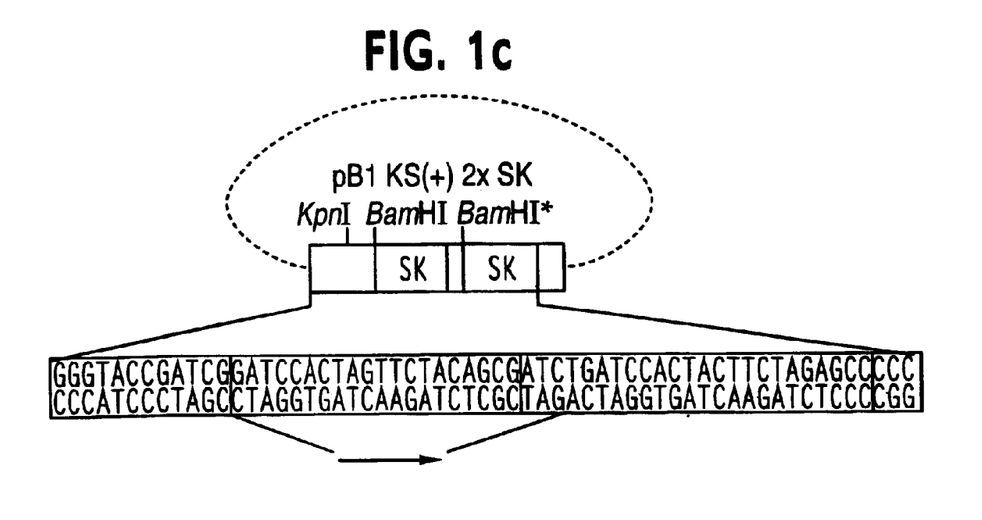
FIG. 1C shows a diagram of pBl KS(+) containing 2 repetitive SK primers (SEQ ID NO:4). pBl KS(+) containing 2 repetitive SK primers is constructed by ligation of SK-PH I with the BamH I/Kpn I digested pBl KS(+) (also see FIG. 1B). The modified BamH I restriction site, marked by an asterisk, could no longer be excised by BamH I. SK primer and non-hybridizing sequences are indicated by an arrow. This leads to the schematic plan for pBl KS(+) containing 2 repetitive SK primers as shown in FIG. 1D.
Figure 1D:
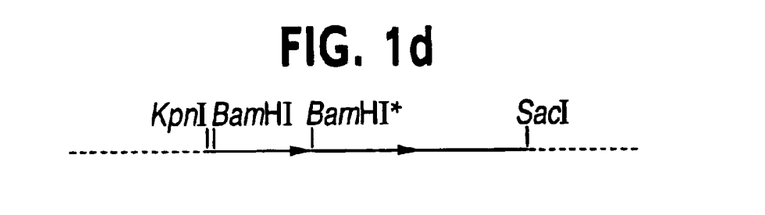
Figure 2:
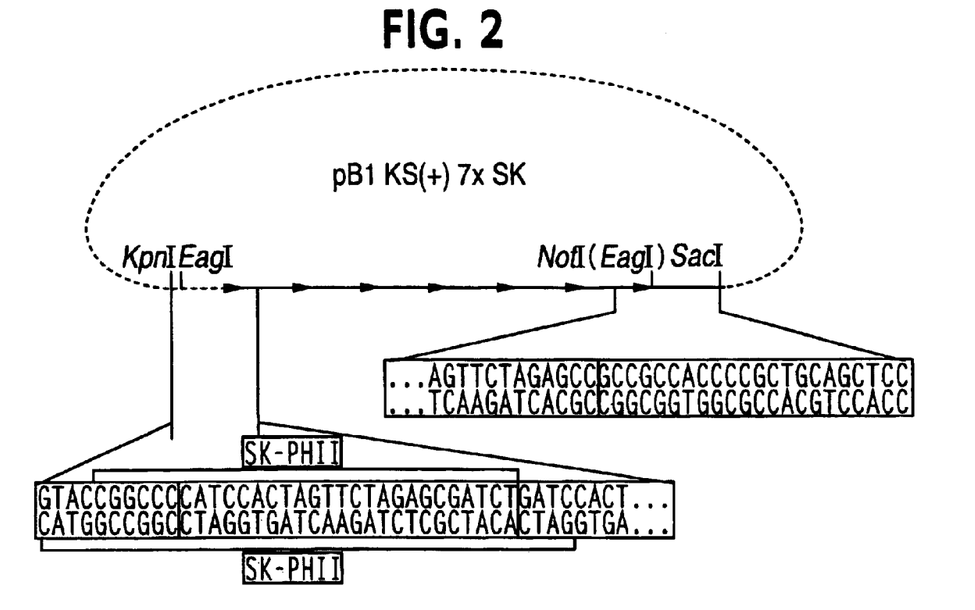
FIG. 2 shows a simplified diagram of vector pBl KS(+) containing 7 repetitive Sk primers (SEQ ID NOs:10 and 11). The pBl vector is marked by a broken line; seven SK primer sequences are located at Kpn I/Sac I-oriented MCS. The SK-PH II fragment (dotted arrow on the top and the sequence of "SK-PH II" is emphasized by lines at the bottom) inserted the seventh SK primer and the additional Eag I restriction site in the vector. Restriction sites are marked on the sequence.

For the production of the plasmid pBl KS(+) (pBluescript KS(+)) with two SK primers (pBl KS(+)2× SK), the pBl KS(+) had to be digested using BamH I and Kpn I, part of the multiple cloning site MCS having been removed (FIG. 1A). The complete double digest was identified on a 2% agarose gel, followed by ethanol precipitation. The insert SK-PH 1 (FIG. 1B) was added to the digested vector for ligation in a tenfold excess (FIG. 1B). This high excess could be justified since the 5' ends of the fragment were not phosphorylated, i.e. oligomers of the inserts could not form. The transformation in E. coli, e.g. XL1 -Blue, was carried out using this ligation batch. Of the raised colonies the plasmid DNA was isolated by mini-preparation from three clones for cloning control. The resulting clones are indicated below as pBl KS(+) 2× SK (FIG. 1C).

The further cloning of plasmids with up to seven SK elements contained in equal orientation was time-consuming, since one clone from the last cloning run served in each case as a basis for the next cloning step. Correspondingly, the mini-prep-DNA of the select pBl 2× SK clone was again double-digested by BamH I/Kpn I and admixed with SK-PH I, ligated and transformed in E. coli XL1-Blue. Contrary to the strategy used for cloning pBl 2× SK, attention had then to be paid especially to an efficient double digest using BamH I and Kpn I. As shown in FIG. 1C, the restriction sites into which another SK-PH I fragment should be integrated, were only six base pairs apart from one another. Such a small distance between two restriction sites does not permit the simultaneous restriction of both restriction sites. Correspondingly, the restriction had to be carried out successively using the two enzymes. Cloning up to the plasmid pBl KS(+) 6× SK was carried out in this way.

To clone the seventh SK primer sequence, the repetitive elements were replicated block-wise. This could only function with a restriction site separating the region with seven SK primers as a unit from the vector. This was enabled by ligation of the SK-PH II (FIG. 2) in pBl 6× SK. Along with the seventh SK element, SK-PH II introduced the new restriction site Eag I into the vector. The seven SK primers were then confined by two Eag I restriction sites (FIG. 2) because the starting vector pBl KS(+) already had such a restriction site in the MCS.

In order to accelerate the further cloning steps, the block-wise replication of the SK elements was made by means of polymerase chain reaction (PCR). The plasmid preparation from XL1-Blue was taken as a template DNA for the amplification of the fragment with seven repetitive elements. It was derived directly from the original colony (pBl 7× SK). At first, to optimize the PCR, primer pair used to amplify the target fragment should be analyzed for quality and quantity. The primers M13, M13 reverse, T3 and T7 (M13: TGTAAAACGACGGCCAGT (SEQ ID NO:6); M13 reverse: CAGGAAACAGCTATGACC (SEQ ID NO.7); T3: AATTAACCCTCACTAAAGGG (SEQ ID NO:8); T7: TAATACGACTCACTATAGGG (SEQ ID NO:9)) were tested in various combinations. All of these primers had their binding sites outside the MCS, either close to the β-galactosidase starting point or close to the T7 transcription starting point in pBluescript KS (+). PCR were performed under standard conditions. Various batches containing matching primers in the various combinations included, M13/M13 reverse, T7/T3, T7/M13 reverse and T3/M13. All of the four primers were combined without the template in the negative control. Since the PCR batch supplied the best results with T3/T7, this primer pair was used for the PCR.

Figure 3A:
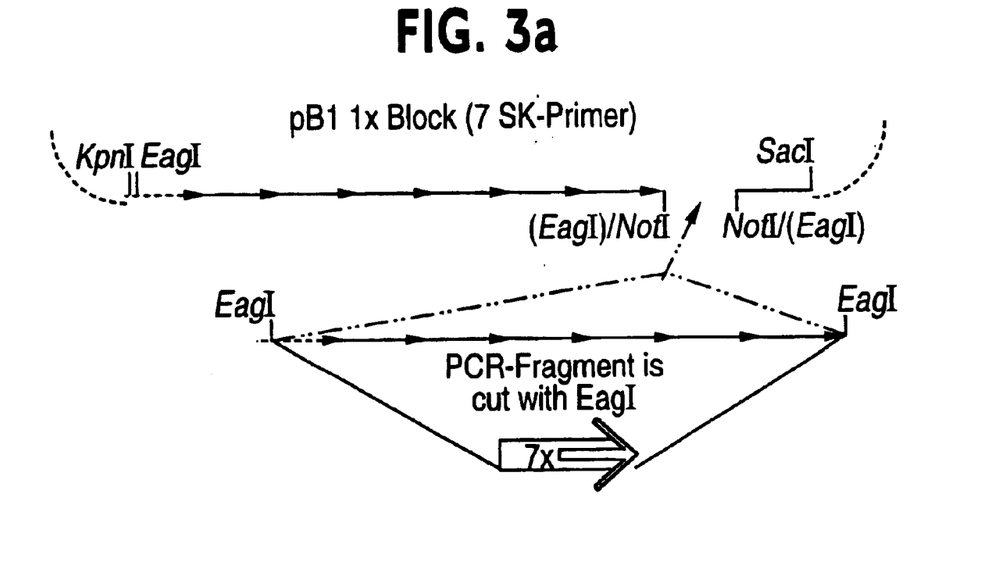
Figure 3B:
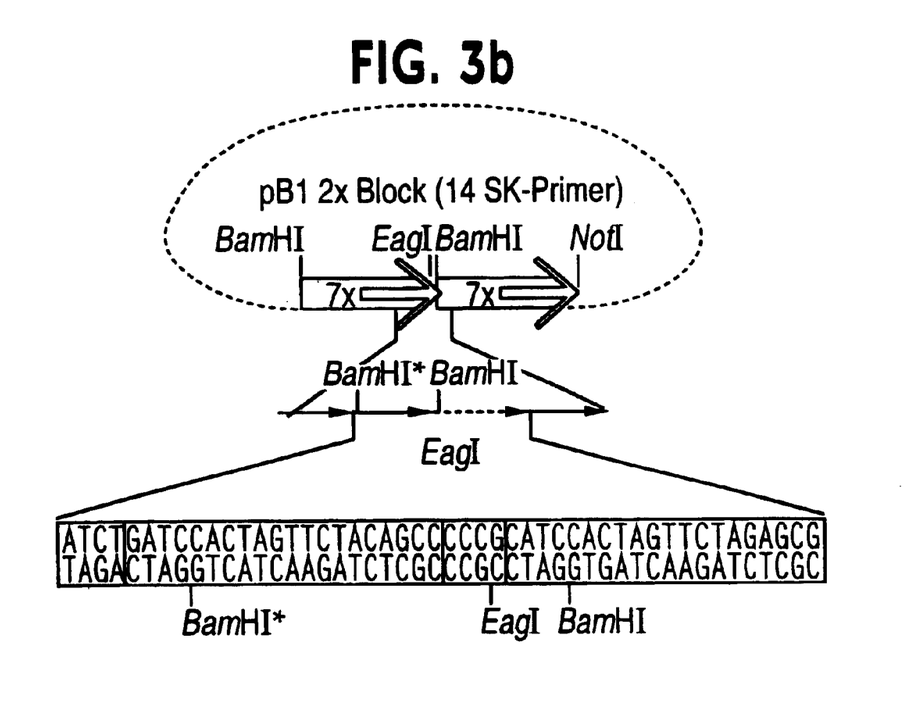

In order to be able to ligate the insert fragment obtained by means of PCR into the NotI-digested vector, Not I compatible sticky ends are needed. For this purpose, the PCR fragment which contained the seven SK primers had to be subsequently cut at the edges. The restriction enzyme Eag I shortened the 246 bp long PCR fragment whose edges were closed to the sequences of primers T3/T7 by 47 bp / 51 bp, respectively. This difference with respect to the control could still be made visible using a 2.2% gel. pBl KS(+) 7× SK changed into pBl KS(+) 14× SK in only one step using the PCR-amplified 7× SK fragment whose edges became compatible with Not I by Eag I digest. See FIGS. 3A and 3B for an outline of the cloning strategy. The digested fragment was purified prior to ligation by the PCR purification kit (Qiagen company). This should serve for removing the unused primers in the PCR reaction and the fragments resulting from the digestion.

As compared to the first cloning steps, which resulted in pBl KS(+) 7× SK, the vector was not digested by two different enzymes (Kpn I/BamH I; see FIG. 1) but linearized by Not I. Therefore, an accumulation of religations had to be expected. In this cloning, a religation could not be counteracted by an insert concentration increased many times over (7× SK fragment), since the DNA blocks were phosphorylated at their 5' ends and uncontrollable oligomerizations of the insert DNA had to be expected. Therefore, the religations were reduced, or even suppressed, by dephosphorylating the vector. The DNA pBl KS(+) 7× SK, as described above, is designated as the pBl 1× block below.

The pBl 1× block digested opened by Not I was ligated with the purified PCR fragment which also contained seven SK primers. This was enabled by the single Not I restriction site located at the edge of the repetitive elements, by which the pBl 1× block was linearized. As mentioned above, the PCR fragment was subsequently cut with the Eag I enzyme compatible with Not I and ligated directly to the seven SK primers of the vector (pBl 2× block).

Since pBl 7× SK proved to be stable in the JM110 host strain, the ligation batch of the plasmid with 14 SK elements was also transformed into this strain. The transformation of pBl KS(+) 14× SK in JM110 yielded 118 transformants. This corresponded to a transformation rate of $1.7 \times 10^3$ cfu (colony forming: units)/ μg DNA.

Step-wise replication was used, in this case with the aim of building up with the 7× SK blocks a plasmid having 28 repetitive SK primer sequences. For this, the pBl 2× block was linearized by Not I as shown analogously in FIGS. 3A & 3B. The full digest was examined on a 1% agarose gel. The 5' ends of this Not I- digested plasmid were dephosphorylated and ligated with the 7× SK block. Seven colonies resulted from this transformation.

Control digest with BamH I of several candidate clones showed that a complete 7× SK block had additionally been inserted. One of the clones was replicated for a mini preparation and the DNA was prepared. The sequence analysis from this mini preparation identified the complete and correct sequence of 21 SK primers including the functioning restriction sites which were required for subsequent cloning run. The gel analyses were confirmed in this connection. This clone is referred to as pBl 3× block below. It served as a precursor for subsequent insertion run.

In order to obtain a plasmid having 28 repetitive SK elements, the block-wise replication of the 7× SK block was continued. The pBl 3× block was used as a starting plasmid of this cloning. This cloning was treated like the two preceding ones. The pBl 3× block was linearized using Not I, checked for full digest in a 1: % agarose gel and then dephosphorylated. The dephosphorylated vector was used together with the PCR-amplified and subsequently cut 7× SK block in a ligation batch. The control ligation for evaluating the dephosphorylation yielded 2 clones. A total of 59 clones were formed in the transformation of the ligation with insert, 16 colonies of which were selected for a mini preparation. Separation with an agarose gel after Sac I/Kpn I digest was made as usual on a 2.2% gel matrix.

A total of 5 clones had prolonged insert regions. Control digests with BamH I and triple digests with Sac I/Kpn I/BamH I showed fragment patterns indicating that no complete 7× SK block might have joined. A BamH I site must have been deleted in the newly joined block during the cloning instead.

Figure 4:
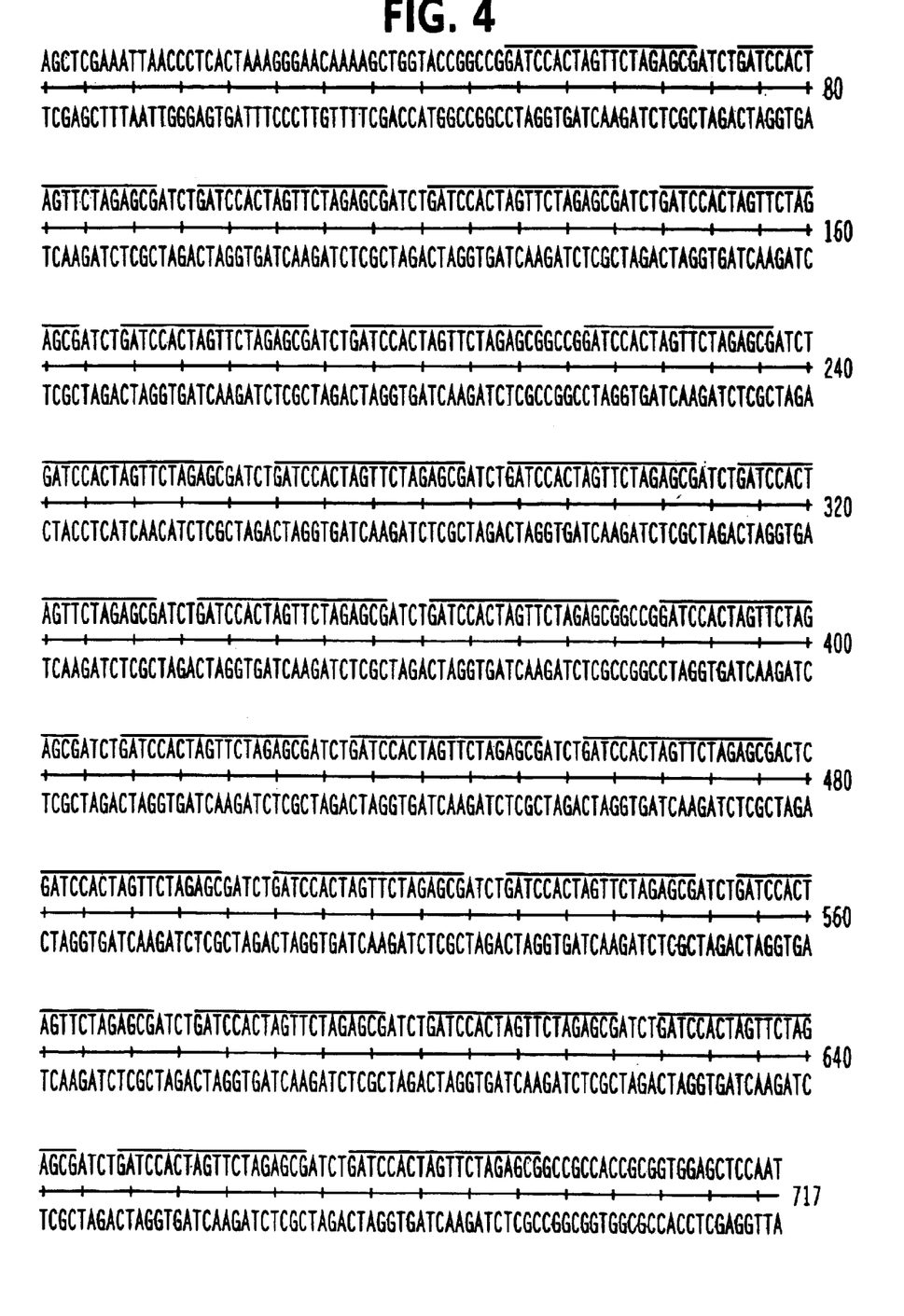
FIG. 4 shows the resulting sequence of the plasmid construct containing 27 repetitive SK primer elements (SEQ ID NO:1). Solid lines on the top indicate the SK primer sequence regions in the repetitive region, which are sequenced from both ends. Sequences ATCT or GCCG having a length of 4 base pairs are located between these SK primer sequence regions for reasons of cloning technique.
Figure 5:
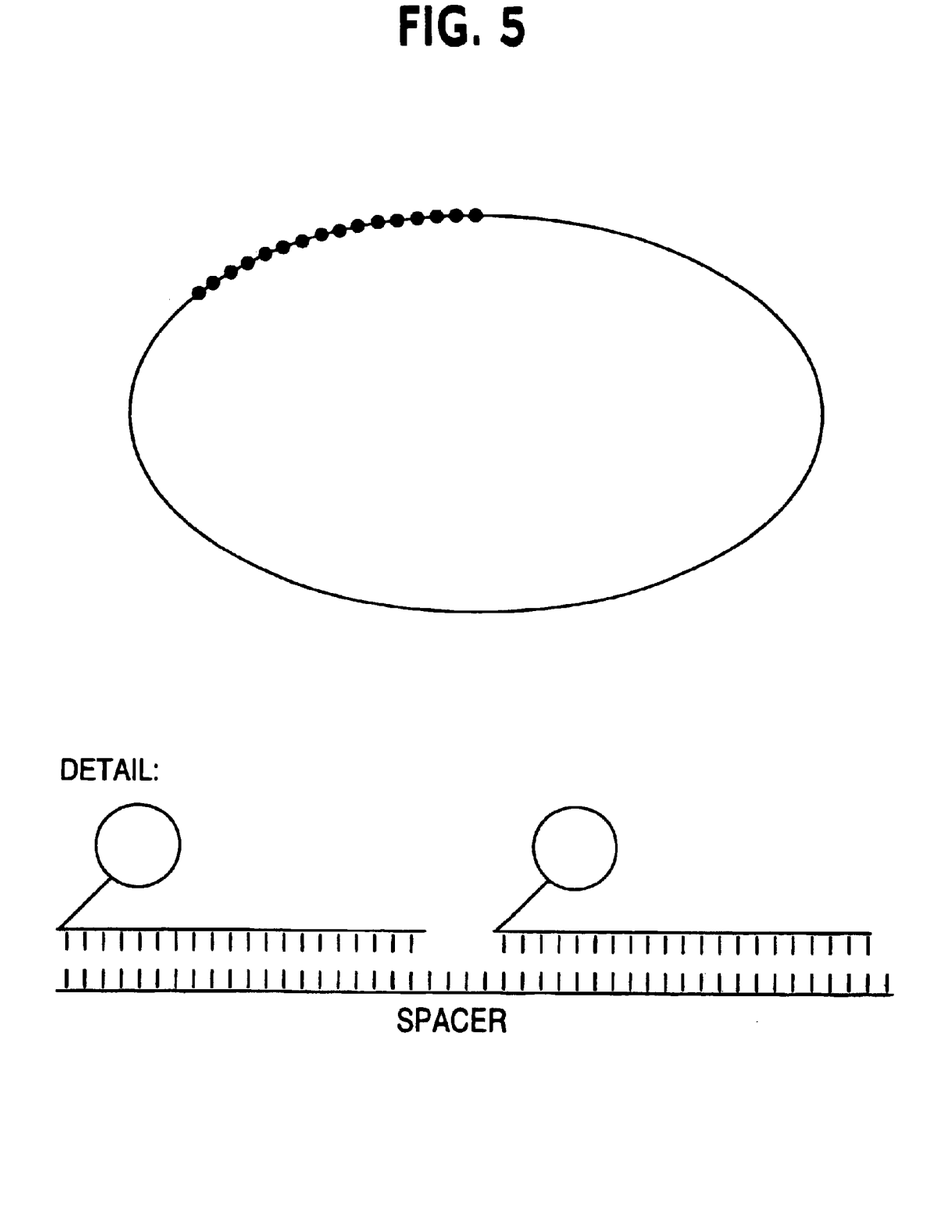
FIG. 5 shows, as an outline, an overall diagram of a plasmid (Solid circular line) that contains 16 repetitive SK primers (16 small solid circles), to which ESI markers bind; and, in greater detail, a diagram of two 20-nucleotide long repetitive SK primer fragments (the lower strand) that are separated by a spacer of a 4-oligonucleotide long fragment (see a gap on the lower strand). ESI markers (the solid balls) are covalently bonded with the single-stranded oligonucleotides (upper strands). The oligonucleotides (upper strands) are bound by complementary base pairing (as a result of hybridization) of the repetitive SK primer fragments (the lower strand) on the plasmid.

One of the five equal clones was chosen and a sequence analysis was made using its mini-prepared DNA. Sequencing confirmed the result that the newly joined BamH I restriction site was deleted. The complete SK primer with intact BamHI restriction site of the last joined 7× SK block lacked. The result was a pBl KS(+) plasmid having 27× SK primers. The sequence of this clone is shown in FIG. 4.

What is claimed is:

1. A plasmid comprising a vector pBluescript KS(+) derivative, wherein the vector contains more than 1 repetitive SK primer sequence element.

2. The plasmid of claim 1, wherein the vector pBluescript KS(+) derivative comprises 2, 7, 14, 21 or 27 repetitive SK primer sequence elements.

3. The plasmid of claim 1, wherein a hybridizing sequence comprising a detectable element is bound to the SK primer sequence elements.

4. The plasmid of claim 1 wherein SK oligonucleotides which are modified at their end with a detectable element can be bound thereto and said detectable element is detectable by electron microscopy.

5. The plasmid of claim 1 wherein the detectable element is selected from the group consisting of boron, silicon, iron and manganese.

6. A reagent for electron microscopy comprising a pBluescript KS(+) derivative that comprises a multiple SK primer sequence element; and a SK oligonucleotide with end modification by a detectable element, wherein the element is detectable by electron microscopy.

7. The reagent of claim 6, wherein the detectable element is selected from the group consisting of boron, silicon, iron and manganese.

8. A host cell transformed with the plasmid of claim 1.

9. The host cell of claim 8, wherein the cell is *E. coli*.

10. The host cell of claim 8, wherein the host cell is *E. coli* JM110.

11. A test kit for use in electron microscopy comprising:
 a) host *E. coli* JM110 bacterial cells suitable for replicating the plasmid of claim 1; and
 b) a single-stranded plasmid comprising at least one of 2, 7, 14, 21, and 27 repetitive SK primer sequence elements.

12. A method of analytical electron microscopy, comprising the steps:
 a) providing the plasmid of claim 1;
 b) adding SK oligonucleotides comprising a detectable element to the plasmid, thereby forming a plasmid-marker complex; and
 c) imaging the complex by electron microscopy.

* * * * *